United States Patent [19]
Takada et al.

[11] Patent Number: 6,113,941
[45] Date of Patent: *Sep. 5, 2000

[54] SUBSTAINED RELEASE MICROCAPSULE OF PHYSIOLOGICALLY ACTIVE COMPOUND WHICH IS SLIGHTLY WATER SOLUBLE AT PH 6 TO 8

[75] Inventors: Shigeyuki Takada, Kobe; Yasushi Nakagawa, Kawanishi; Susumu Iwasa, Kyoto, all of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/569,097

[22] PCT Filed: Sep. 21, 1995

[86] PCT No.: PCT/JP95/01905

§ 371 Date: Dec. 22, 1996

§ 102(e) Date: Dec. 22, 1996

[87] PCT Pub. No.: WO96/10397

PCT Pub. Date: Apr. 11, 1996

[30] Foreign Application Priority Data

Sep. 30, 1994 [JP] Japan ................................... 6-237948

[51] Int. Cl.⁷ ...................................................... A61K 9/52
[52] U.S. Cl. .......................... 424/451; 424/489; 424/426; 424/490; 514/963
[58] Field of Search ............................ 514/963; 424/451, 424/489, 426, 490; 264/4.32, 4.6

[56] References Cited

FOREIGN PATENT DOCUMENTS

| | | |
|---|---|---|
| 0325199 | 7/1989 | European Pat. Off. . |
| 0350246 | 1/1990 | European Pat. Off. . |
| 0357061 | 3/1990 | European Pat. Off. . |
| 0359036 | 6/1990 | European Pat. Off. . |
| 0386667 | 9/1990 | European Pat. Off. . |
| 0415294 | 3/1991 | European Pat. Off. . |
| 0535937 | 4/1993 | European Pat. Off. . |
| 0586238 | 3/1994 | European Pat. Off. . |
| 0586838 | 3/1994 | European Pat. Off. . |
| 911359 | 9/1991 | WIPO . |

OTHER PUBLICATIONS

Pharaceutical Research, N. Ammoury et al., vol. 8, No. 1, Jan. 1991, "Jejunal Absorption, Pharmacological Activity, and Pharmacokinetic Evaluation of Indomethacin–Loaded Poly (d,1–Lactide) and Poly (Isobutyl–Cyanoacrylate) Nanocapsules in Rats".

Science, J. Folkman et al., pp. 719–725, Aug. 1983, "Angiogenesis Inhibition and Tumor Regression Caused by Heparin or a Heparin Fragment in the Presence of Cortisone".

*Primary Examiner*—Raj Bawa
*Attorney, Agent, or Firm*—Fitzpatrick, Cella, Harper & Scinto

[57] ABSTRACT

A pharmaceutical preparation is provided by a microcapsule containing a physiologically active substance which is water-soluble only at a pH of about 3 or below, and a polymer which is biodegradable upon oral administration. A process for producing the microcapsule is also provided.

20 Claims, No Drawings

SUBSTAINED RELEASE MICROCAPSULE OF PHYSIOLOGICALLY ACTIVE COMPOUND WHICH IS SLIGHTLY WATER SOLUBLE AT PH 6 TO 8

TECHNICAL FIELD

The present invention relates to a microcapsule using a biodegradable polymer to encapsulate a physiologically active substance.

BACKGROUND OF THE INVENTION

In general, drugs that are slightly water-soluble at pH 6 to 8 are slightly absorbed into the digestive tract after oral administration because of their low dissolution rates. In order to improve the solubility of the drugs, the slightly water-soluble drugs have been formulated as readily water-soluble salts, or a solution adjuvant is introduced as an additive. However, in the case of hydrochloric acid salts for example, hydrochloric acid sometimes separates from the hydrochloric acid salt during storage. When a solution adjuvant is added, the resulting tablets contain so many ingredients and sometimes become so large that it becomes difficult to take them. In addition, because the acid that is added as an additive readily dissolves and disappears, the effects of improving the solubility also disappear.

Pharmaceutical Research, Vol. 8, No. 1, p. 101 (1991) reports studies on nanocapsules which contain the slightly water-soluble drug indomethacin. However, indomethacin is not readily soluble in water at a pH no higher than 3. In addition, no improvement in the absorption of the drug has been achieved in the study.

DISCLOSURE OF THE INVENTION

The present inventors have designed and studied a microcapsule containing a physiologically active substance that is soluble in water at a pH no higher than about 3 by using a biodegradable polymer as a base. As a result, it has been found that a microcapsule prepared by adding to a biodegradable polymer a physiologically active substance that is water-soluble at a pH no higher than about 3 and dissolving the mixture in an organic solvent gradually releases a water-soluble low molecular weight free acid and the physiologically active substance at the same time after degradation of the base occurs in the digestive tract after oral administration. It has also been found that the microcapsule solubilizes a physiologically active substance that is normally insoluble in the digestive tract from the duodenum to the rectum, thereby improving the absorption of the physiologically active substance. After further studies based on these findings, the present invention has been completed.

The present invention provides a microcapsule comprising a physiologically active substance which is water-soluble at a pH no higher than about 3, and a biodegradable polymer.

The present invention also provides a microcapsule which is obtainable by dissolving in an organic solvent a physiologically active substance which is water-soluble at a pH no higher than about 3 together with a biodegradable polymer, and then subjecting the resulting solution to in-water drying or spray drying.

The present invention also relates to a process for producing a microcapsule which comprises dissolving in an organic solvent a physiologically active substance which is water-soluble at a pH no higher than about 3 together with a biodegradable polymer, and then subjecting the resulting solution to in-water drying or spray drying.

The present invention further relates to a method of treating ulcer or hypertension in a mammal which comprises administering to such mammal in need thereof an effective therapeutic amount of the above microcapsule.

The present invention still further relates a method of enhancing absorption of a slightly absorbable physiologically active substance, which comprises encapsulating the slightly absorbable physiologically active substance by dissolving in an organic solvent the slightly absorbable physiologically active substance together with a biodegradable polymer, and then subjecting the resulting solution to in-water drying or spray drying.

The present invention also provides use of a slightly absorbable physiologically active substance and a biodegradable polymer for manufacture of a microcapsule.

The present invention also provides use of the above microcapsule for enhancing absorption of a slightly absorbable physiologically active substance.

The present invention makes it possible to encapsulate a physiologically active substance which is water-soluble at a pH no higher than about 3 into microcapsules by using biodegradable polymers. Further, addition of an appropriate excipient can control the degradation rate of the polymer and the release rate or duration time of the physiologically active substance to be absorbed.

The term "microcapsule" used herein is intended to collectively include microspheres, microcapsules, microparticles, nanoparticles, nanospheres, and nanocapsules.

The physiologically active substance to be used in the present invention is a drug which is readily soluble in water under acidic conditions, in particular at a pH no higher than about 3. Preferably, the physiologically active substance is slightly soluble in water under neutral conditions, in particular at pH 6 to 8. The term "soluble in water" or "water-soluble" used herein regarding the physiologically active substance means that the water-solubility of the physiologically active substance is not less than about 0.01 g, preferably not less than about 1 g, per 100 ml of water at about 20° C. The term "slightly soluble in water" or "slightly water-soluble" used herein regarding the physiologically active substance means that the water-solubility of the physiologically active substance is not more than about 0.01 g, preferably not more than about 0.001 g, per 100 ml of water at about 20° C. Preferably, the physiologically active substance is slightly absorbable, that is, slightly absorbed in the digestive tract from the duodenum to the rectum.

The pharmacological activity of the physiologically active substance is not specifically limited. Examples thereof include antibiotics, antifungal agents, antilipidemic agents, drugs for circulatory systems, anti-platelet aggregation drugs, antitumor agents, antipyretics, analgesics, anti-inflammatory agents, antitussiveexpectorants, sedatives, muscle relaxants, antiepileptic agents, antiulcer agents, antidepressants, antiallergic agents, cardiotonics, antiarrhythmic agents, vasodilators, hypotensive diuretics, antidiabetic agents, anticoagulants, hemostatics, antituberculous agents, hormone preparations, narcotic antagonists, bone resorption inhibitors, angiogenesis inhibitors, etc.

Examples of the antibiotics include gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cefalotin, cefaloridine, cefotiam, cefsulodin, cefmenoxime, cefmetazole, cefazolin, cefotaxime, cefoperazone, ceftizoxime, moxolactam, thienamycin, sulfazecin, azusleonam, etc.

Examples of the antifungal agents include 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)-phenyl]-3(2H,4H)-1,2,4-triazolone, 2-[(1R,2R)-2-(2,4-difluorophenyl)-2-hydroxy-1-methyl-3-(1H-1,2,4-triazol-1-yl)propyl]-4-[4-trifluoromethoxyphenyl]-3(2H,4H)-1,2,4-triazolone, 2-[(1R,2R)-2-(2,4-difluorophenyl)-2-hydroxy-1-methyl-3-(1H-1,2,4-triazol-1-yl)propyl]-4-[4-(2,2,2-trifluoroethoxy)phenyl]-3(2H,4H)-1,2,4-triazolone, etc. In particular, 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone is preferred.

Examples of the antilipidemic agents include pravastatin, simvastatin, etc.

Examples of the drugs for circulatory systems include substituted alanylglycine compounds having angiotensin converting enzyme (ACE) inhibitory activity, such as N-[N-[(S)-1-ethoxycarbonyl-3-phenylpropyl]-L-alanyl]-N-(indan-2-yl)glycine, N-[N-[(S)-1-carboxy-3-phenylpropyl]-L-alanyl]-N-(indan-2-yl)glycine, and N-[N-[(S)-1-carboxy-3-phenylpropyl]-L-alanyl]-N-(5-hydroxyindan-2-yl) glycine. In particular, N-[N-[(S)-1-ethoxycarbonyl-3-phenylpropyl]-L-alanyl]-N-(indan-2-yl)glycine is preferred.

Examples of the anti-platelet aggregation drugs include ticlopidine, cilostazol, alprostadil, limaprost, dipyridamole, ethyl icosapentaenoate, beraprost, ozagrel, aspirin, etc.

Examples of the antitumor agents include bleomycin hydrochloride, methotrexate, actinomycin D, mitomycin C, vinblastine sulfate, vincristine sulfate, daunorubicin hydrochloride, adriamycin, neocarzinostatin, cytosine arabinoside, fluorouracil, tetrahydrofuryl-5-fluorouracil, krestin, picibanil, lentinan, levamisole, bestatin, azimexon, glycyrrhizin, poly I:C, poly A:U, poly ICLC, etc.

Examples of the antipyretics, analgesics and anti-inflammatory agents include sodium salicylate, sulpyrine, sodium flufenamate, diclofenac sodium, indomethacin sodium, morphine hydrochloride, pethidine hydrochloride, levorphanol tartarate, oxymorphone, etc.

Examples of the antitussive expectorants include ephedrine hydrochloride, methylephedrine hydrochloride, noscapine hydrochloride, codeine phosphate, dihydrocodeine phosphate, alloclamide hydrochloride, chlorphezianol hydrochloride, picoperidamine hydrochloride, cloperastine, protokylol hydrochloride, isoproterenol hydrochloride, salbutamol sulfate, terbutaline sulfate, etc.

Examples of the sedatives include chlorpromazine hydrochloride, prochlorperazine, trifluoperazine, atropine sulfate, methylscopolamine bromide, etc.

Examples of the muscle relaxants include pridinol methanesulfonate, tubocurarine chloride, pancuronium bromide, etc.

Examples of the antiepileptic agents include phenytoin sodium, ethosuximide, acetazolamide sodium, chlordiazepoxide hydrochloride, etc.

Examples of the antiulcer agents include benzimidazole compounds having proton pump inhibitory activity (e.g., 2-[[[3-methyl-4-(2,2,3,3-tetrafluoropropoxy)-2-pyridyl] methyl]thio]benzimidazole, 2-[[[3-methyl-4-(2,2,3,3,3-pentafluoropropoxy)-2-pyridyl]methyl]thio]benzimidazole, etc.), metoclopramide, histidine hydrochloride, etc. In particular, 2-[[[3-methyl-4-(2,2,3,3-tetrafluoropropoxy)-2-pyridyl]methyl]thio]benzimidazole, or 2-[[[3-methyl-4-(2,2,3,3,3-pentafluoropropoxy)-2-pyridyl]methyl]thio]-benzimidazole is preferred.

Examples of the antidepressants include imipramine, clomipramine, noxiptilin, phenelzine sulfate, etc.

Examples of the antiallergic agents include imidazopyridazine compounds having antiasthmatic activity (e.g., 3-(imidazo[1,2-b]pyridazine-6-yl)oxy-2,2-dimethylpropane-sulfonamide, etc.), triazolopyridazine compounds having antiasthmatic activity (e.g., 2-ethyl-2-[(7-methyl-[1,2,4]triazolo[1,5-b]pyridazin-6-yl)-oxymethyl]butane-sulfonamide, etc), diphenhydramine hydrochloride, chlorpheniramine maleate, tripelennamine hydrochloride, methdilazine hydrochloride, clemizole hydrochloride, diphenylpyraline hydrochloride, methoxyphenamine hydrochloride, etc. In particular, 3-(imidazo[1,2-b]pyridazine-6-yl)oxy-2,2-dimethylpropane-sulfonamide, or 2-ethyl-2-[(7-methyl-[1,2,4]triazolo[1,5-b]pyridazin-6-yl)-oxymethyl]butanesulfonamide is preferred.

Examples of the cardiotonics include transbioxocamphor, theophyllol, aminophylline, methoxyphenamine hydrochloride, etc.

Examples of the antiarrhythmic agents include propranolol hydrochloride, alprenolol hydrochloride, bufetolol hydrochloride, oxyprenolol hydrochloride, etc.

Examples of the vasodilators include oxyephedrine hydrochloride, diltiazem hydrochloride, tolazoline hydrochloride, hexobendine, bamethan sulfate, etc.

Examples of the hypotensive diuretics include hexamethonium bromide, pentolinium, mecamylamine hydrochloride, ecarazine hydrochloride, clonidine hydrochloride, etc.

Examples of the antidiabetic agents include glymidine sodium, glipizide, phenformin hydrochloride, buformin hydrochloride, metformin, etc.

Examples of the anticoagulants include heparin sodium, sodium citrate, etc.

Examples of the hemostatics include thromboplastin, thrombin, menadione sodium bisulfite, acetomenaphthone, ε-aminocaproic acid, tranexamic acid, carbazochrome sodium sulfonate, adrenochrome monoaminoguanidine methanesulfonate, etc.

Examples of the antituberculous agents include isoniazid, ethambutol, sodium para-aminosalicylate, etc.

Examples of the hormone preparations include prednisolone succinate, prednisolone sodium phosphate, dexamethasone sodium sulfate, betamethasone sodium phosphate, hexoestrol phosphate, hexoestrol acetate, methymazole, etc.

Examples of the narcotic antagonists include levallorphan tartarate, nalorphine hydrochloride, naloxone hydrochloride, etc.

Examples of the bone resorption inhibitors include (sulfur-containing alkyl)aminomethylenebisphosphonic acid, etc.

Examples of the angiogenesis inhibitors include angiostatic steroids, disclosed in Science, 221, 719 (1983), fumagillin, disclosed in EP-A-325,119, fumagillol derivatives (e.g., O-monochloroacetylcarbamoylfumagillol, O-dichloroacetyl-carbamoylfumagillol, etc., (EP-A-357,061, EP-A-359,036, EP-A-386,667, EP-A-415,294), etc.

Of the above physiologically active substances, basic compounds are preferred. In particular, an imidazole or its condensed ring compound, a triazole or its condensed ring compound, or a substituted alanylglycine compound is most preferred. The imidazole or its condensed ring compound is preferably a benzimidazole compound {e.g., 2-[[[3-methyl-4-(2,2,3,3-tetra-fluoropropoxy)-2-pyridyl]methyl]thio]-benzimidazole} or 3-(imidazo[1,2-b]pyridazin-6-yl)oxy-2,2-dimethylpropanesulfonamide. The triazole or its condensed ring compound is preferably 2-ethyl-2-[(7-methyl-[1,2,4]triazolo[1,5-b]pyridazin-6-yl)oxymethyl]-butanesulfonamide, or 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3-(2H,4H)-1,2,4-triazolone. The substituted alanylglycine compound is preferably N-[N-[(S)-1-ethoxycarbonyl-3-phenylpropyl]-L-alanyl]-N-(indan-2-yl)glycine.

The amount of the physiologically active substance to be used varies depending upon such factors as a particular kind of substance, desired pharmacological activity, etc. When water/oil (w/o) type emulsions are prepared, the concentration of the physiologically active substance in the aqueous phase is about 0.001% to about 90% (W/W), preferably about 0.01% to about 80% (W/W).

The biodegradable polymer to be used in the present invention is a biocompatible polymer which is degradable in living bodies and slightly soluble or insoluble in water.

Examples of the biodegradable polymers include poly fatty acid esters (e.g., polylactic acid, polyglycollic acid, polycitric acid, polymalic acid, polylactic acid caprolactone), poly-α-cyanoacrylic acid esters, polyhydroxybutyric acid (e.g., poly-β-hydroxybutyric acid), polyalkylene oxalates (e.g., polytrimethylene oxalate, polytetramethylene oxalate), poly ortho esters, poly ortho carbonates and other polycarbonates (e.g., polyethylene carbonate, polyethylenepropylene carbonate), polyamino acids (e.g., poly-γ-benzyl-L-glutamic acid, poly-L-alanine, poly-γ-methyl-L-glutamic acid), hyaluronic acid esters, etc. These polymers may be used alone or in combination thereof. They may be used in the form of a copolymer or a mixture of two or more polymers. They may also be in the form of salts thereof.

In particular, poly fatty acid esters are preferred. More preferred polymers are polylactic acid, lactic acid/glycolic acid copolymers, hydroxybutyric acid/glycolic acid copolymers (e.g., β-hydroxybutyric acid/glycolic acid copolymers), butyric acid/glycolic copolymers or mixtures thereof of the above, lactic acid/glycollic acid copolymers, and hydroxybutyric acid/glycolic acid copolymers are particularly preferred.

The weight-average molecular weight of the biodegradable polymer is preferably selected from the range of about 1,000 to about 20,000, more preferably about 2,000 to about 8,000. In particular, fatty acid polyesters having a weight-average molecular weight selected from the above range are preferred.

The molecular weight used herein is a molecular weight indicated as the molecular weight of polystyrene which is determined by gel permeation chromatography (GPC) using polystyrene as a standard material. The determination was carried out using GPC column TSK gel (2000, 2500, 3000; manufactured by Tosoh, Japan) and chloroform as the mobile phase.

The composition ratio of the copolymer, e.g., lactic acid/ glycollic acid copolymer or hydroxybutyric acid/glycollic acid copolymer is preferably about 100/0 to 25/75 (W/W; lactic acid or hydroxybutyric acid/glycolic acid), is more preferably about 75/25 to 25/75 (W/W).

The amount of the biodegradable polymer to be used depends upon various factors such as the degree of the pharmacological activity, release rate, and duration time of the physiologically active substance. For example, the polymer is used as the microcapsule base in an amount of about 0.2 to 10,000 times (by weight), preferably about 1 to 100 times (by weight), of the weight of the physiologically active substance.

The hydrolysis of the biodegradable polymer can be accelerated at a low or high pH. Therefore, acidic or basic excipients can be used in order to modulate the polymer erosion rate. The excipients can be mixed in a solid form with the physiologically active substance or dissolved in an organic solvent containing the polymer. The amount of the excipients should be between 0.1% and 30% (weight relative to the polymer weight). Examples of the excipients include inorganic acids such as ammonium sulfate and ammonium chloride, organic acids such as citric acid, benzoic acid, heparin and ascorbic acid, inorganic bases such as sodium carbonate, potassium carbonate, calcium carbonate, zinc carbonate and zinc hydroxide, organic bases such as protamine sulfate, spermine, choline, ethanolamine, diethanolamine and triethanolamine, and surfactants such as TWEEN™ (polyoxyethylenesorbitan fatty acid ester) and PLURONIC™ (polyoxyethylene-polyoxypropylene copolymer).

The concentration of the biodegradable polymer in the oil phase is selected from the range of about 0.5 to about 90% (W/W), preferably between about 2 to about 60% (W/W).

The above polymer-containing solution (oil phase) is a solution of a polymer in an organic solvent.

The organic solvent is not specifically limited so long as it has a boiling point no higher than about 120° C. and is slightly miscible with water and dissolves the biodegradable polymer. Examples of the organic solvents include halogenated alkanes (e.g., dichloromethane, chloroform, chloroethane, trichloroethane, carbon tetrachloride, etc.), ethyl acetate, ethyl ether, cyclohexane, benzene, n-hexane, toluene, etc. These solvents can be mixtures of two or more solvents.

The microcapsule of the present invention can be prepared, for example, by subjecting a solution of the above physiologically active substance and the above biodegradable polymer in an organic solvent to in-water drying, spray drying or phase separation. Initially, the physiologically active substance and the polymer are dissolved in an organic solvent. In order to adjust the biodegradation rate of the polymer, an aqueous solution of a pH adjustor may be added, followed by emulsification to prepare a w/o type emulsion. The pH adjustors include carbonic acid, acetic acid, oxalic acid, citric acid, tartaric acid, succinic acid, phosphoric acid or their sodium or potassium salts, hydrochloric acid, sodium hydroxide, etc.

The emulsification can be carried out by conventional dispersion techniques such as intermittent shaking, mixing by means of a mixer (e.g., propeller agitator, turbine agitator, etc.), colloid mill operation, mechanical homogenization, ultrasonication, etc.

When the physiologically active substance is insoluble, it is subjected to fine-granulation to prepare a solid/oil (s/o) type emulsion.

Then, the w/o type emulsion, oil phase solution, or s/o type emulsion thus obtained is subjected to in-water drying to prepare microcapsules. When the microcapsules are prepared by an in-water drying process, the w/o type emulsion, oil phase solution, or s/o type emulsion is further added to the third phase (aqueous phase) to form a w/o/w type, o/w type or s/o/w type emulsion, followed by removal of the solvent in the oil phase to prepare microcapsules.

An emulsifying agent may be added to the outer phase (aqueous phase). In general, any emulsifying agent can be used so long as it forms a stable o/w type emulsion. Examples of the emulsifying agents include anionic surfactants (e.g., sodium oleate, sodium stearate, sodium laurate); nonionic surfactants such as polyoxyethylenesorbitan aliphatic acid esters (e.g., TWEEN 80, TWEEN 60 (Atlas Powder Co.)), polyoxyethylene castor oil derivatives (e.g., HCO-60, HCO-50 (Nikko Chemicals)), polyvinyl pyrrolidone, polyvinyl alcohol, carboxymethyl cellulose, lecithin, gelatin, etc. These emulsifying agents can be used alone or in combination thereof. The concentration of the emulsifying agent to be used is selected from the range of about 0.01% to about 20% (W/W), preferably about 0.05% to 10% (W/W).

The solvent in the oil phase can be removed by. conventional methods, for example, by stirring with a propeller-type stirrer, magnetic stirrer, etc., under atmospheric pressure or gradually reduced pressure, or by evaporating the solvent while controlling degree of vacuum by using a rotary evaporator, etc. In this case, when solidification of the polymer proceeds to some degree and the loss of the physiologically active substance caused by its release from the internal phase is decreased, a w/o/w type, o/w type or s/o/w type emulsion may be warmed gradually to remove the solvent completely. This warming operation shortens the time for removing the solvent.

The microcapsules thus obtained are collected by centrifugation or filtration. Then, the free physiologically active substance, carriers for the substance, etc., attached onto the surface of the microcapsules are washed off with distilled water repeatedly several times. Water in the microcapsules and the solvent in the microcapsules are completely dried under reduced pressure, if necessary, with warming.

When the microcapsules are prepared by the phase separation process, the coacervation agent below is gradually added with stirring to the w/o type or s/o type emulsion or the oil phase to precipitate and solidify the polymer.

Any coacervation agent can be used so long as it is a polymeric, mineral-oil or vegetable-oil compound which is miscible with a solvent for the polymer and which does not dissolve a polymer for encapsulation. The coacervation agents include, for example, silicone oil, sesame oil, soybean oil, corn oil, cottonseed oil, coconut oil, linseed oil, mineral oil, etc. These coacervation agents can be used as mixtures thereof.

The microcapsules thus obtained are collected by filtration, and then repeatedly washed with heptane, etc., to remove the coacervation agent. The free physiologically active substance and solvent are removed in a similar manner to that in the in-water drying process. In order to prevent aggregation of the particles during the washing, an aggregation preventing agent may be added.

The microcapsules thus obtained are screened, if necessary after light pulverization, to remove microcapsules that are too large.

When the microcapsule of the present invention is produced by a spray drying process, the organic solvents to be used for the oil phase may be the above-mentioned solvent or a solvent that is readily miscible with water, such as acetone, acetonitrile, tetrahydrofuran, dioxane, pyridine, alcohols (e.g., methanol, ethanol), etc. These solvents can be used as mixtures thereof. An appropriate mixing ratio of a mixture of water with the above organic solvent which homogeneously dissolves the physiologically active substance and the polymer may be used.

Then, the w/o type emulsion or s/o type suspension or solution thus obtained is sprayed into a drying chamber of a spray dryer through a nozzle, and the organic solvent and water in the atomized droplets are volatilized in a very short time to prepare powdery microcapsules. The nozzle may be a two-liquid type nozzle, pressure type nozzle, rotary disc type nozzle, etc. At the same time, in order to prevent aggregation of the microcapsules, an aqueous solution of an aggregation-preventing agent is sprayed from another nozzle. That is, the spray dryer is provided with two nozzles, and the w/o type emulsion, s/o type suspension or physiologically active substance/polymer solution is sprayed from one nozzle, while a suitable amount of an aqueous solution of an aggregation-preventing agent is sprayed from the other nozzle to form coating on the surface of the microparticles. When a two-liquid nozzle or pressure nozzle is used as the nozzle, the two nozzles may be provided in the center of the spray dryer. Preferably, a nozzle having the structure for two-liquid spraying are used so that the physiologically active substance/polymer solution and the aqueous solution of the aggregation-preventing agent can be sprayed separately without mixing them in the nozzles.

The aggregation-preventing agents include water-soluble inorganic salts, organic acids and organic acid salts. They are not specifically limited so long as they can be administered to human bodies and are solid non-adherent substance at room temperature. The inorganic salts include, for example, alkaline metal halides (e.g., sodium chloride, potassium chloride, sodium bromide, potassium bromide, etc.), alkaline earth metal halides (e.g., calcium chloride, magnesium chloride, etc.), ammonium halides (e.g., ammonium chloride, ammonium bromide, etc.), alkaline metal carbonates or bicarbonates (e.g., sodium carbonate, potassium carbonate, sodium bicarbonate, potassium bicarbonate, etc.), alkaline earth metal carbonates (e.g., calcium carbonate, magnesium carbonate, etc.), ammonium carbonate, ammonium bicarbonate, alkaline metal phosphates (e.g., sodium phosphate, potassium phosphate, disodium hydrogenphosphate, dipotassium hydrogenphosphate, sodium dihydrogenphosphate, potassium dihydrogenphosphate, etc.), diammonium hydrogenphosphate, ammonium dihydrogenphosphate, alkaline earth metal oxides (e.g., magnesium oxide, calcium oxide, etc.), alkaline earth metal hydroxides (e.g., magnesium hydroxide, calcium hydroxide, etc.), etc.

The water-soluble organic acids include, for example, citric acid, tartaric acid, malic acid, succinic acid, benzoic acid, chondroitin sulfate, dextran sulfate, carboxymethylcellulose, alginic acid, pectic acid, etc.

The water-soluble organic acid salts include, for example, salts of acetic acid, citric acid, tartaric acid, malic acid, succinic acid, benzoic acid, chondroitin sulfate, dextran sulfate, carboxymethylcellulose, alginic acid, pectic acid, carbonic acid, bicarbonic acid, etc., with an alkaline metal (e.g., sodium, potassium, etc.), ammonium, basic amino acid or alkaline earth metal salt (e.g., calcium, magnesium, etc.).

In particular, water-soluble inorganic salts are preferred. These water-soluble inorganic salts, organic acids and organic acid salts can be used alone or in combination thereof in an appropriate ratio.

The formulation ratio of the above water-soluble inorganic salt, organic acid or organic acid salt based on the polymer may be in the range in which aggregation-preventing effect is observed. For example, the ratio by weight is about 0.001 to about 100, preferably about 0.01 to about 50, more preferably about 0.1 to about 10

In the present invention, a surfactant may be contained in the aggregation-preventing agent solution and may be sprayed with the physiologically active substance/polymer solution. Alternatively, it may be sprayed with the physiologically active substance/polymer solution through a nozzle other than that for the aggregation-preventing agent. Thus, the surfactant is dispersed on the surface of the microcapsule preparation, or the surface of the microcapsule preparation is coated with the surfactant. This provides very high dispersibility when the microparticle preparation is dispersed in a dispersive medium.

Preferred examples of the surfactants include nonionic surfactants such as alkylene glycols (e.g., propylene glycol, etc.), polysorbates (e.g., polysorbate 40, polysorbate 60, polysorbate 80, etc.), macrogols (e.g., macrogol 300, macrogol 400, macrogol 600, macrogol 1500, macrogol 4000, macrogol 6000, etc.), polyoxyethylene hardened castor oil (e.g., polyoxyethylene hardened castor oil 10, polyoxyethylene hardened castor oil 50, polyoxyethylene hardened castor oil 60,), etc. These surfactants can be used alone or in combination thereof in an appropriate mixing ratio.

The formulation ratio of the above surfactant based on the polymer is not specifically limited so long as it is in the range in which improved dispersibility is observed. For example, the ratio by weight is about 0.0000001 to about 10, preferably about 0.000005 to about 5, more preferably about 0.00001 to about 0.01.

Water in the microcapsules and the solvent in the microcapsule membrane are completely removed under reduced pressure, if necessary, with warming.

The microcapsules of the present invention can be administered as they are or after processing them into various preparations orally, intrarectally, or directly into organs.

The above preparations include oral preparations (e.g., powders, granules, capsules, tablets), suppositories (e.g., rectal suppositories, vaginal suppositories), injections, etc. In particular, oral preparations are preferred.

The microcapsules of the present invention can be processed into tablets according to conventional methods. For example, to the microcapsules are added an excipient (e.g., lactose, crystalline cellulose, sucrose, starch such as corn starch, etc.), a disintegrating agent (e.g., starch such as corn starch, croscarmellose sodium, carboxymethylstarch sodium, calcium carbonate, etc.), a binder (e.g., crystalline cellulose, acacia, dextrin, carboxymethylcellulose, polyvinyl pyrrolidone, hydroxypropylcellulose, etc.) or a lubricant (e.g., talc, magnesium stearate, polyethylene glycol 6000, etc.), etc. Then the mixture is compressed for shaping.

The microcapsules of the present invention can be processed into oily or aqueous solid suppositories, semi-solid or liquid suppositories by per se known methods. The oleaginous bases for the above composition are not specifically limited so long as they do not dissolve the microcapsules. Examples thereof include higher fatty acid glycerides [e.g., cacao butter, Witepsol (Dynamit-Nobel, Germany), etc.], intermediate fatty acids [e.g., Miglyol (Dynamit-Nobel), etc.], vegetable oils (e.g., sesame oil, soybean oil, cottonseed oil, etc.), etc. The aqueous bases include, for example, polyethylene glycol and propylene glycol. The aqueous gels include, for example, natural gum, cellulose derivatives, vinyl polymers, polyacrylates, etc.

When the microcapsules of the present invention are processed into, for example, injections, the microcapsules are dispersed in an aqueous vehicle together with a dispersing agent (e.g., TWEEN 80, HCO-60 (manufactured by Nikko Chemicals), carboxymethylcellulose, sodium alginate, etc.), a preservative (e.g., methylparaben, propylparaben, benzyl alcohol, chlorobutanol, etc.), a tonicity agent (e.g., sodium chloride, glycerin, sorbitol, glucose, etc.), etc., to prepare aqueous suspensions. They may also be dispersed in a vegetable oil (e.g., olive oil, sesame oil, peanut oil, cottonseed oil, corn oil, etc.), propylene glycol, etc., to prepare oily suspensions. In this manner, sustained release injections can be prepared.

The microcapsules of the present invention can be used for treating various diseases such as ulcer, hypertension, asthma, hyperlipemia, bacterial or fungal infections, tumor, inflammatory diseases, epilepsy, depression, allergic diseases, arrhythmia, diabetes, tuberculosis, osteoporosis, etc., in mammals such as mice, rats, horses, cattle, humans, etc., depending upon. pharmacological activity of the physiologically active substance. Preferably, the microparticules of the present invention are used for treating ulcer or hypertension.

The effective therapeutic dose of the microcapsules or their preparations of the present invention varies depending upon such factors as the kind and content of physiologically active substance as an active ingredient, dosage forms, duration of the release, recipient animals and purposes of treatment. It is important to ensure that the effective dose of the active ingredient will be administered. For example, the unit dose for a human may be selected from the range of about 1 mg to 10 g, preferably about 10 mg to 2 g, calculated as the weight of the microcapsules. Preferably, the microcapsules of the present invention are used in a sustained-release preparation.

The microcapsules of the present invention have, for example, the following advantages:

(1) The microcapsules can improves absorption of a physiologically active substance which is slightly soluble and slightly absorbable into the digestive tract from the duodenum to the rectum. That is, the biodegradable polymer contained in the microparticles as a base degrades in the digestive tract after administration of the microcapsules to gradually release a free acid of a water-soluble low molecular weight molecule (monomer to oligomer) together with a physiologically active substance. Thus, the physiologically active substance which does not normally dissolve in the digestive tract is solubilized by the released acid, and thus its absorption can be improved.

(2) Sustained release microcapsules particularly for oral administration can be prepared from a slightly water-soluble physiologically active substance by using a biodegradable polymer having varying biodegradation rates. Further, addition of an appropriate additive can control the degradation rate of the biodegradable polymer and the release rate and duration time of the physiologically active substance.

(3) When a readily soluble salt such as hydrochloric acid salt is used to improve the solubility of physiologically active substances as in prior art techniques, hydrochloric acid separates from the hydrochloric acid salt during storage. However, the biodegradable polymers in the present invention do not cause such a problem.

(4) When additives such as acids are added as solution adjuvants, the acids readily dissolve and disappear and solubilization effects are not obtained. On the other hand, the solubility of the biodegradable polymers in the present invention can be controlled.

(5) The microcapsules can be produced by an in-water drying process, phase separation process, spray drying process, etc. These processes can be controlled to provide homogeneously spherical microcapsules having a particle size of 0.1 to 1000 $\mu$m.

(6) In a spray drying process, microcapsules having a high drug content of 10 to 50% can be prepared in a short period of time.

The following examples further illustrate the present invention in detail but are not to be construed to limit the scope thereof. In the examples, all the percents (%) are indicated as weight/weight percents.

EXAMPLE 1

The antiulcer drug 2-[[[3-methyl-4-(2,2,3,3,-tetrafluoropropoxy)-2-pyridyl]methyl]thio]benzimidazole (hereinafter sometimes referred to as Compound A) (400 mg) and lactic acid/glycollic acid copolymer (lactic acid/glycollic acid=50/50, average molecular weight calculated as polystyrene=5400) (3.6 g) were dissolved in dichloromethane (5 ml) to prepare an o/w type emulsion using a homogenizer in an aqueous solution (800 ml) of 0.1% polyvinyl alcohol (PVA). Then, the emulsion was slowly stirred with a conventional propeller stirrer. After dichloromethane vaporized and the microcapsules hardened, the microcapsules were collected by centrifugation and at the same time washed with purified water. The collected microcapsules were freeze-dried for a day to obtain powdery microcapsules.

The drug content in the total amount of the microcapsules was 10.0%, and the entrapment was 100%. The microcapsules were suspended in 0.5% methylcellulose, and orally administered to SD-strain male rats (body weight: 250 g) in a dose of 20 mg/kg. A suspension of the drug alone in 0.5% methylcellulose was also administered for comparison. In both cases, the plasma concentration of the drug and the absorption ratio were determined. The results are shown in Table 1.

TABLE 1

| Orally administered suspension | $C_{max}$ ($\mu$g/ml) | $T_{max}$ (hr) | Absorption ratio (%) |
|---|---|---|---|
| Suspension of Compound A in 0.5% methylcellulose | 0.218 | 0.25 | 5.4 |
| Suspension of microcapsules | 0.423 | 1.5 | 27.0 |

The results show that the oral microcapsule preparation significantly improved $C_{max}$ (peak blood level), $T_{max}$ (time required to obtain the peak blood level) and the absorption ratio. In other words, the oral administration of the suspension of Compound A in 0.5% methylcellulose provided a low administration ratio of 5.4% because Compound A has a very low solubility at the pH in the small intestine, whereas the lactic acid/glycollic acid copolymer microcapsules increased the absorption ratio because they released lactic acid or glycollic acid together with the drug in the small intestine and the drug was, therefore, present in solubilized form. In addition, $T_{max}$ was prolonged six times, and the prolonged release was achieved.

EXAMPLE 2

Compound A (500 mg) and lactic acid/glycollic acid copolymer (lactic acid/glycollic acid=50/50, average molecular weight calculated as polystyrene=5400) (4.5 g) were dissolved in dichloromethane (7 ml), and citric acid buffer (pH 3) (0.5 ml) was added and mixed for about 30 seconds with a small homogenizer (Polytron, manufactured by Kinematica, Switzerland) to give a w/o type emulsion. From this emulsion, a w/o/w type emulsion was prepared using a homogenizer in 0.5% PVA aqueous solution (1000 ml). Then, the emulsion was slowly stirred with a conventional propeller stirrer for 3 hours. After dichloromethane vaporized while w/o type microcapsules hardened, the microcapsules were centrifuged and collected and at the same time washed with purified water. The collected microcapsules were freeze-dried for a day to obtain powdery microcapsules.

The drug content in the microcapsules was 9.9%, and the entrapment was 99%. The microcapsules were suspended in 0.5% methylcellulose, and orally administered to SD-strain male rats (body weight: 250 g) in a dose of 20 mg/kg. For comparative purposes, a suspension of the drug alone in 0.5% methylcellulose was also administered. In both cases, the plasma concentration of the drug and the absorption ratio were determined. The results are shown in Table 2.

TABLE 2

| Orally administered suspension | $C_{max}$ ($\mu$g/ml) | $T_{max}$ (hr) | Absorption ratio (%) |
|---|---|---|---|
| Suspension of Compound A in 0.5% methylcellulose | 0.218 | 0.25 | 5.4 |
| Suspension of microcapsules | 0.713 | 3.0 | 42.1 |

The results show that the oral microcapsule preparation significantly improved $C_{max}$, $T_{max}$ and the absorption ratio. In other words, the oral administration of the lactic acid/glycollic acid copolymer microcapsules provided a significantly improved absorption ratio and prolonged release of the drug compared to the suspension of Compound A in 0.5% methylcellulose.

EXAMPLE 3

The antiulcer drug 2-[[[3-methyl-4-(2,2,3,3,3-pentafluoropropoxy)-2-pyridyl]methyl]thio]benzimidazole(1 g) and polylactic acid (molecular weight: 6000) (9 g) were dissolved in acetonitrile (30 ml). The solution was sprayed from one two-fluid nozzle which was provided in a spray dryer, and at the same time 5% mannitol aqueous solution was sprayed from another two-fluid nozzle. Thus, powdery microcapsules were obtained. The temperature at the entrance of the drying chamber was 100° C., the temperature at the outlet was 50° C., and the flow rate was 10 ml/min.

EXAMPLE 4

The antiasthmatic drug 2-ethyl-2-[(7-methyl-[1,2,4]triazolo[1,5-b]pyridazin-6-yl)oxymethyl]-butanesulfonamide (3 g), polyhydroxybutyric acid/glycollic acid copolymer (hydroxybutyric acid/glycollic acid=60/40, average molecular weight calculated as polystyrene=7000) (5 g) and polylactic acid (molecular weight: 6000) (4 g) were dissolved in a mixture of ethanol (10 ml) and acetonitrile (30 ml). The solution was sprayed from a rotary disc atomizer provided in a spray dryer to obtain powdery microcapsules. The temperature at the entrance of the drying chamber was 100° C., the temperature at the outlet was 50° C., and the flow rate was 10 ml/min.

EXAMPLE 5

The angiotensin converting enzyme inhibitor N-[N-[(S)-1-ethoxycarbonyl-3-phenylpropyl]-L-alanyl]-N-(indan-2-yl)glycine (1 g) and polyhydroxybutyric acid/glycollic acid copolymer (hydroxybutyric acid/glycollic acid=40/60, average molecular weight calculated as polystyrene=7000) (5 g) were dissolved in dichloromethane (6 ml). From this solution, an o/w type emulsion was prepared using a homogenizer in 0.1% PVA aqueous solution (500 ml). Then, the emulsion was slowly stirred with a conventional propeller stirrer for 3 hours. After dichloromethane vaporized and the microcapsules hardened, the microcapsules were collected by centrifugation and at the same time washed with purified water. The collected microcapsules were freeze-dried for a day to obtain powdery microcapsules.

What is claimed is:

1. A sustained release pharmaceutical microcapsule comprising:

a basic physiologically active compound which is soluble in 20° water at a pH of about 3 or less but not more than about 0.01 g of said compound is soluble in 100 ml of 20° C. water at pH to 8, wherein said basic physiologically active compound comprises a moiety selected from the group consisting of imidazole, benzimidazole, triazole and alanylglycine, and a polymer having a weight-average molecular weight in the range of about 2,000 to about 8,000, said polymer being biodegradable in the digestive tract of a mammal from the duodenum to the rectum upon oral administration.

2. The microcapsule according to claim 1, wherein the biodegradable polymer is a poly fatty acid ester.

3. The microcapsule according to claim 1, wherein the biodegradable polymer is lactic acid/glycolic acid copolymer.

4. The microcapsule according to claim 3, wherein the composition ratio of lactic acid/glycolic acid is 100/0 to 25/75 (weight/weight).

5. The microcapsule according to claim 1, wherein the biodegradable polymer is hydroxybutyric acid/glycolic acid copolymer.

6. The microcapsule according to claim 5, wherein the composition ratio of hydroxybutyric acid/glycolic acid is 100/0 to 25/75 (weight/weight).

7. The microcapsule according to claim 1, wherein the water-solubility of the physiologically active compound is not less than about 1 g/100 ml at 20° C. and pH 3 or less.

8. The microcapsule according to claim 1, wherein the physiologically active compound is a benzimidazole compound.

9. The microcapsule according to claim 8, wherein the benzimidazole compound is 2-[[[3-methyl-4-(2,2,3,3-tetrafluoropropoxy)-2-pyridyl]methyl]thio]benzimidazole.

10. The microcapsule according to claim 1, wherein the physiologically active compound is 3-(imidazo[1,2-b] pyridazin-6-yl)oxy-2,2-dimethylpropanesulfonamide.

11. The microcapsule according to claim 1, wherein the physiologically active compound is 2-ethyl-2-[(7-methyl-[1,2,4]triazolo[1,5-b]pyridazin-6-yl)oxymethyl]-butanesulfonamide.

12. The microcapsule according to claim 1, wherein the physiologically active condensed ring compound is 2-[(1R, 2R)-2-(2,4-difluorophenyl)-2-hydroxy-1-methyl-3-(1H-1,2,4-triazol-1-yl)propyl]-4-[4-(2,2,3,3-tetrafluoropropoxy) phenyl]-3-(2H,4H)-1,2,4-triazolone.

13. The microcapsule according to claim 1, wherein the physiologically active compound is N-[N-[(S)-1-ethoxycarbonyl-3-phenylpropyl]-L-alanyl]-N-(indan-2-yl) glycine.

14. The microcapsule according to claim 1, which is for treating ulcer.

15. The microcapsule according to claim 1, which is for treating hypertension.

16. A microcapsule according to claim 1, which is prepared by dissolving said physiologically active substance and said biodegradable polymer in an organic solvent, and then subjecting the resulting solution to in-water drying or spray drying.

17. A process for producing a microcapsule according to claim 1, which comprises dissolving said physiologically active substance and said biodegradable polymer in an organic solvent, and then subjecting the resulting solution to in-water drying or spray drying.

18. A method of treating ulcer in a mammal which comprises administering to such mammal in need thereof an effective amount of a microcapsule according to claim 1.

19. A method of treating hypertension in a mammal which comprises administering to such mammal in need thereof a therapeutically effective amount of a microcapsule as claimed in claim 1.

20. A method administering a physiologically active substance to a mammal in need thereof, comprising:

orally administering to said mammal a therapeutically effective amount of a microcapsule according to any one of claims 1–6, 7, 8–13 or 14–16, whereby absorption of said physiologically active substance in said digestive tract is enhanced.

* * * * *

UNITED STATES PATENT AND TRADEMARK OFFICE
CERTIFICATE OF CORRECTION

PATENT NO.     : 6,113,941
DATED          : September 5, 2000
INVENTOR(S)    : Shigeyuki Takada et al.

Page 1 of 1

It is certified that error appears in the above-identified patent and that said Letters Patent is hereby corrected as shown below:

Column 2,
Line 54, "antitussiveexpectorants," should read -- antitussive expectorants, --.

Column 5,
Line 43, "acid/glycollic" should read -- acid/glycolic --; and
Line 61, "glycollic" (both occurrences) should read -- glycolic --.

Column 7,
Line 16, "by." should read -- by --.

Column 8,
Line 67, "10" should read -- 10. --.

Column 10,
Line 32, "improves" should read -- improve --.

Column 11,
Lines 13, 14, 51, 53, 59, and 60, "glycollic" should read -- glycolic --.

Column 12,
Line 50 and 51, "glycollic" should read -- glycolic --.

Column 14,
Line 9, "condensed ring" should be deleted; and
Lines 42, "claims 1-6, 7, 8-13 or 14-16," should read -- claims 1-16, --.

Signed and Sealed this

Eighteenth Day of December, 2001

*Attest:*

JAMES E. ROGAN
*Attesting Officer*        *Director of the United States Patent and Trademark Office*